US006622719B1

(12) United States Patent
Slautterback et al.

(10) Patent No.: US 6,622,719 B1
(45) Date of Patent: Sep. 23, 2003

(54) HERNIA BRIEF

(75) Inventors: Ernest Gerald Slautterback, Coral Springs, FL (US); Rhonda M. Machin, Weston, FL (US); Jennifer L. Miller, Plantation, FL (US); Daniel J. Bozza, Coral Springs, FL (US)

(73) Assignee: FLA Orthopedics, Inc.

( * ) Notice: Subject to any disclaimer, the term of this patent is extended or adjusted under 35 U.S.C. 154(b) by 0 days.

(21) Appl. No.: 10/292,032

(22) Filed: Nov. 12, 2002

(51) Int. Cl.[7] .................................................. A61F 5/24
(52) U.S. Cl. ........................................ 128/98.1; 602/67
(58) Field of Search ............................... 128/95.1, 96.1, 128/98.1; 602/67–73

(56) References Cited

U.S. PATENT DOCUMENTS 1,612,121 A * 12/1926 Hittenberger
3,524,449 A * 8/1970 Peters
3,754,549 A * 8/1973 Nelkin
4,416,272 A * 11/1983 Nelkin ........................ 128/96.1
4,957,105 A * 9/1990 Kurth .......................... 128/96.1

* cited by examiner

Primary Examiner—Michael A. Brown

(57) ABSTRACT

Disclosed is an improved hernia device which includes an undergarment brief having front, side, rear and crotch portions defining spaced leg openings wherein the front portion has one or two truss pads supported from its inner surface to protrude inwardly of the brief to engage and support abdominal hernia areas of the body of a wearer; with the truss pads independently held in position and urged toward the body of the wearer by a pair of straps having inner ends secured to the center of the front portion and extending in opposite directions with distal ends independently and adjustably secured to side portions forward of opposite lateral side centers of the hips of the wearer. Also disclosed is the use of a two piece seat or rear panel having a heavier upper portion of heavier material which assists in providing back support while carrying and distributing tension which may be transferred by the tension straps. A further feature of the device is the provision the convenience of dual toilet access openings from said crotch portion.

10 Claims, 4 Drawing Sheets

HERNIA BRIEF

This invention relates to hernia supports or trusses, and in particular, to a combination brief or undergarment and hernia support which provides both support and comfort to a wearer.

BACKGROUND OF THE INVENTION

Many devices have been employed and proposed for the wearer's relief and comfort from reducible inguinal hernias. Predominantly these devices have been in the form of belts or trusses, while others have taken the form of briefs or undergarments which include a combined hernia support. However, the combined type devices which have heretofore been available have tended to be uncomfortable to wear, have provided insufficient or improperly directed support to the hernia area, or have lacked a capability for providing effective and convenient user control of the degree of support in plural areas. Illustrative examples of prior combined type devices appear in the following United States Patents:

U.S. Pat. No. 4,416,272, issued Nov. 22, 1983 to Nelkin, describes a combination underpant and hernia truss which comprises a brief having front, rear and crotch portions with spaced leg holes and a waist opening having a waist band. A truss pad is attached to the front portion and protrudes inwardly of the brief to engage and support a herniated abdominal area. An adjustable length belt encircles the brief and the wearer, and is connected to the center of the front portion of the brief adjacent the pad, for directing hernia retaining force on the pad. Provision is made for both left and right truss pads. The encircling belt is free from securement to other portions of the brief and may be moved and positioned upwardly and downwardly by the wearer. The device thus constitutes in essence a complete brief in addition to a largely separate hernia belt. The belt encircles the body of the wearer with the loose belt ends being fastened together at the wearer's back. When it is thus secured, its diameter forms in effect a second waistband which tends to cause discomfort while at the same time providing a limited nature and degree of hernia retaining support adjustability.

U.S. Pat. No. 4,671,264, issued Jun. 9, 1987, to Frangi, describes an underpant brief and hernia truss. An elastic belt is disposed at the circumferential upper edge of the brief, and a pair of at least partly elastic bands has upper ends which are affixed to the elastic belt and pass laterally of the crotch of the pant, adjacent the leg holes of the brief. These bands include an inelastic segment on the front of the underpant extending diagonally across hernia affected regions of the wearer. Pockets are included over the hernia affected region for receiving a retaining pad. The assembled and finished garment is essentially an integrated one piece garment. The dimensions and securements of the sewn together layers are fixed at the time of manufacture, whereby the fit and support provided by the garment are not susceptible of user adjustment.

U.S. Pat. No. 3,454,003, issued Nov. 22, 1977, to Kleber-Sailhen, describes a brief-like undergarment for hernia patients. The garment is multi-layered, wherein the inner front and rear portions are provided with reinforcements. These reinforcements comprise a front ventral girdle which is joined at its ends to a back pelvic portion. Both reinforcements are stitched to the respective front and back garment portions which they reinforce. Hernia pad pockets are provided at the inner surface of the front reinforced garment portion. Adjustable tensioning is applied to the inner surfaces of the hernia pad pockets by two elastic thigh straps which extend slidably through the hems outlining the leg openings of the brief-like garment. Each thigh strap is fixedly attached at one end to either the front or rear inside of the composite garment, while its other end is adjustably attached to the opposing portion of the garment. This adjustability entails changing the lengths of the elastic straps extending between the legs of the wearer.

While these prior devices purport to serve their intended purposes, for the most part, their designs are such as to produce a significant degree of complexity of manufacture, fit, and adjustment and/or discomfort for the wearer.

SUMMARY OF THE INVENTION

The present invention relates to a hernia brief which comprises an undergarment in the form of an elastic brief having one or more abdominal pockets for receiving one or more pads (right or left, or right and left), adapted to provide the desired hernia support. A pair of external front tension control straps is attached to a front central portion of the brief and the straps extend outwardly therefrom in opposite directions. The straps extend over the abdominal pockets and their enclosed pads and have distal ends which are adapted to be adjustably attached to outside surfaces of frontal areas of the brief on the other sides of the pockets. The points of attachment of the distal ends are independently adjustable and are preferably disposed on side portions of the brief forward of oppositely disposed lateral side centers of the hips of the wearer.

This arrangement eliminates the need for a torso encircling circumferential strap, allows a range of sizing, provides more accurate and precise individual pad adjustment, and provides wearer comfort. The adjustability of fastening is preferably achieved in a convenient fashion through hook and loop securements of the strap ends to frontal or side areas of the brief whereby the discomfort of multiple torso encircling waist bands is avoided. The unique arrangement also provides a garment fit which is largely independent of the adjustment of the support provided by the pads. Another feature of the invention is the use of a two piece seat or rear panel having an upper portion of heavier material which assists in providing back support while carrying and distributing tension which may be transferred by the tension straps. A still further feature of the device of the invention is the provision the convenience of dual toilet access openings through use of a novel but simple arrangement of a minimum of elements. This arrangement of the hernia brief facilitates efficiency and economy of manufacture It is a primary of object of the present invention to provide an improved hernia brief, which eliminates or alleviates the shortcomings of the foregoing exemplar hernia devices described in the patent literature.

It is another object of the invention to provide such an improved hernia device which provides easy, individualized, and precise adjustment, is comfortable to the wearer, and which provides an adjustable fit for different waist sizes.

It is another object of the invention to provide an improved hernia device which is comprised of an undergarment brief having front, side, rear and crotch portions defining spaced leg openings, wherein the front portion has one or two truss pads supported from its inner surface to protrude inwardly of the brief to engage and support abdominal hernia areas of the body of a wearer, with the truss pads independently held in position and urged toward the body of the wearer by a pair of straps having inner ends secured to the center of the front portion and extending in opposite directions with distal ends independently and adjustably secured to the side portions forward of opposite lateral side centers of the hips of the wearer.

Other objects and advantages of this invention will become apparent from the following description taken in connection with the accompanying drawings wherein are set forth, by way of illustration and example, certain embodiments of this invention.

DESCRIPTION OF THE PREFERRED EMBODIMENT

Figure 1:
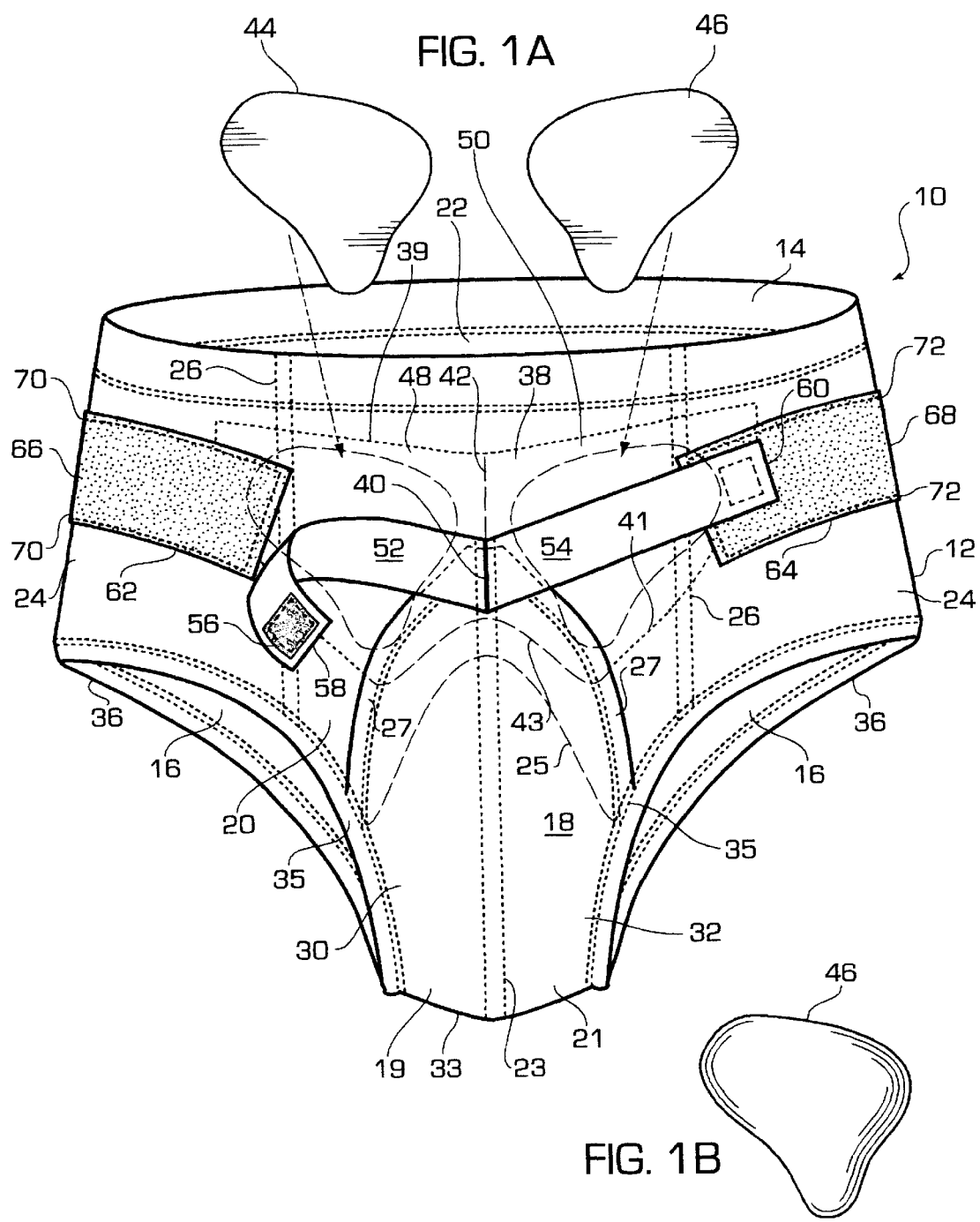
FIG. 1A is a front perspective view of a preferred embodiment of a hernia brief embodying the present invention.
FIG. 1B is a plan perspective view of a hernia pad suitable for use in the device of the invention, showing in particular its convexly contoured surface.

As required, a detailed embodiment of the present invention is disclosed herein, however, it is to be understood that the disclosed embodiment is merely exemplary of the invention which may be embodied in various forms, therefore, specific structural and functional details disclosed herein are not to be interpreted as limiting, but merely as a basis for the claims and as a representative basis for teaching one skilled in the art to variously employ the present invention in varying appropriate structures.

Referring to the drawings in more detail, there is seen at 10 a depiction of a combination brief and an integrated hernia support. The brief 12 has an elastic waist band 14, leg openings 16, and crotch 18. The crotch 18 comprises a conventional pouch formed of two halves 19 and 21 sewn together along the vertical center seam 23 and having side edges hemmed at 27. The body 12 of the brief is formed of a front panel 20, a rear panel 22, and two side panels 24. The side panels 24 join the two vertical side edges of the front panel 20 to the two vertical side edges of the rear panel 22. See FIGS. 1A and 2. These four panels 20, 22, and 24, are fastened together by any suitable means, such as by sewing. The sewn joinder of the vertical edges of the front, side and rear panels is indicated in the drawings by the generally vertical broken line seams 26 and 28. The seams 26 between the front panel 20 and the side panels 24 overlie the abdomen of a wearer. The seams 28 between the rear panel 22 and the side panels 24 lie substantially along the lateral side centers of the hips of a wearer. The upper horizontal edges of the front, side, and rear panels terminate in the elastic waistband 14. Lower edges of the front, side and rear panels 20, 22, and 24 and crotch 18 define the perimeters of the leg openings or holes 16. The central portion of the lowermost edge of the front panel 20 is upwardly cut away at 25 for a purpose presently to become apparent. This lower front panel edge is seen in phantom in FIGS. 1A and 4.

The lowermost horizontal or lateral edges of the pouch halves 19 and 21 of the crotch 18 are sewn to the center lower horizontal or lateral edge of the rear panel 22 along a generally horizontal lateral seam 33, which is seen in FIG. 1A. This seam extends laterally between the perimeters of the leg openings or holes 16. The upper end of the vertical crotch seam 23 is sewn to the center of the front panel 20 by a short vertical seam shown at 40. The upper hemmed edges 27 of the crotch pouch halves 19 and 21 are unattached to the front panel 20. However, the lowermost side edges 27 of the crotch pouch halves 19 and 21 which intersect the leg openings 16, are securely sewn to the lowermost outer edges of the front panel 20 on both sides of the cut away 25, as indicated at 35. The unattached status of the hemmed edges 27 of the crotch pouch halves 19 and 21 between the seams 35 and 40, and the cutaway portion 25 of the front panel 20, provide convenient toilet access openings for the wearer. The leg openings or holes 16 are preferably finished by conventional hems 36 around their perimeters. As stated, these perimeters are bordered by lower edges of the side and rear panels, the crotch, and the opposed outer corners of the lower edge of the front panel at the points where these corners are secured to the outer edges of the crotch.

The brief is preferably formed of a supportive elastic material, such as that which is manufactured under the registered trademark SPANDEX, and provides a comfortable, lightweight, cool, washable material with elasticity to provide inward pressure and support for the wearer's body.

Figure 4:
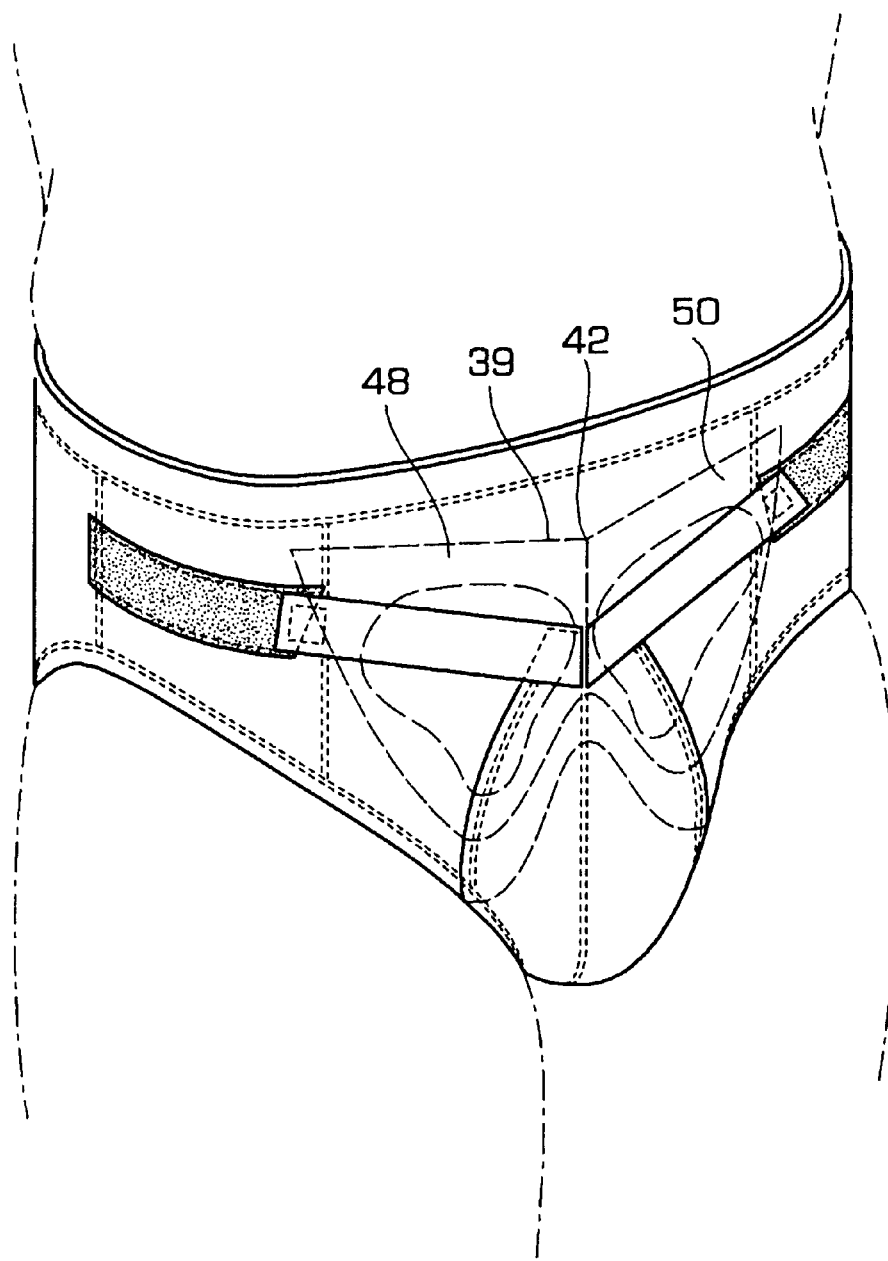
FIG. 4 is a front and side perspective view of the hernia brief of FIGS. 1A through 3 on the body of a wearer, showing in phantom the hernia pads and pad pockets.

Referring to FIGS. 1A and 4, pockets for hernia pads are formed on the inner surface of the forward portion of the brief by the attachment thereto of a pocket panel 38. The pocket panel 38 is seen in phantom in FIGS. 1A and 4. The panel 38 is generally the shape of a truncated inverted triangle having a shallow V shaped upper edge 39, from which it tapers downward to form a scalloped lower edge 41 having a central cutaway 43. The lateral center of the pocket panel 38 may be sewn to the front panel 20, as shown by the vertical broken line 42 in FIGS. 1A and 4. The depending lower edge 41, 43 of the pocket panel is sewn to the front panel 20 to form the pockets 48 and 50. The shallow V shaped upper edge 39 of the pocket panel 38 is unattached to the brief to provide access to the pockets.

Referring to FIGS. 1A and 1B, one or two hernia pads 44 and 46 may be inserted in the pockets 48 and 50, depending on the need and preference of the wearer. This is best illustrated in phantom in FIGS. 1A and 4. The hernia pads may be of a generally kidney shape having a substantially flat outer surface, which is seen in FIG. 1A, and a contoured inner surface, which is illustratively shown in FIG. 1B. It will be understood that the contoured inner surface is the surface which is urged towards and into engagement with the body of the user. Further illustration of typical pads of this type is provided in the assignee's U.S. Pat. No. 6,422, 242, issued to Slautterback, et al. Jul. 23, 2002, which is incorporated herein by reference.

It is a feature of the unique hernia brief of the invention that it is provided with a new and unusually advantageous arrangement for adjustably applying pressure to the pads to tailor the combined brief and hernia support to the anatomy, needs and preferences of each individual user. Referring particularly to FIG. 1A, a pair of tension straps 52 and 54 have their centermost inner ends fastened to the front of the brief 12 substantially along its center line, as by sewing to the outside of the crotch pouch along the seam 40. From this attachment the straps 52 and 54 extend outwardly and slightly upwardly in opposite directions. In this arrangement the tension straps pass over the major lobes of the kidney shaped hernia pads 44 and 46. The distal ends 58 and 60 of the straps 52 and 54 are provided on their inner surfaces with securing patches 56, which may be of a hook and loop fastening fabric such as that marketed under the registered trademark VELCRO of the American Velcro Company. The tension straps 52 and 54 are preferably provided with a degree of longitudinal elasticity.

Figure 2:
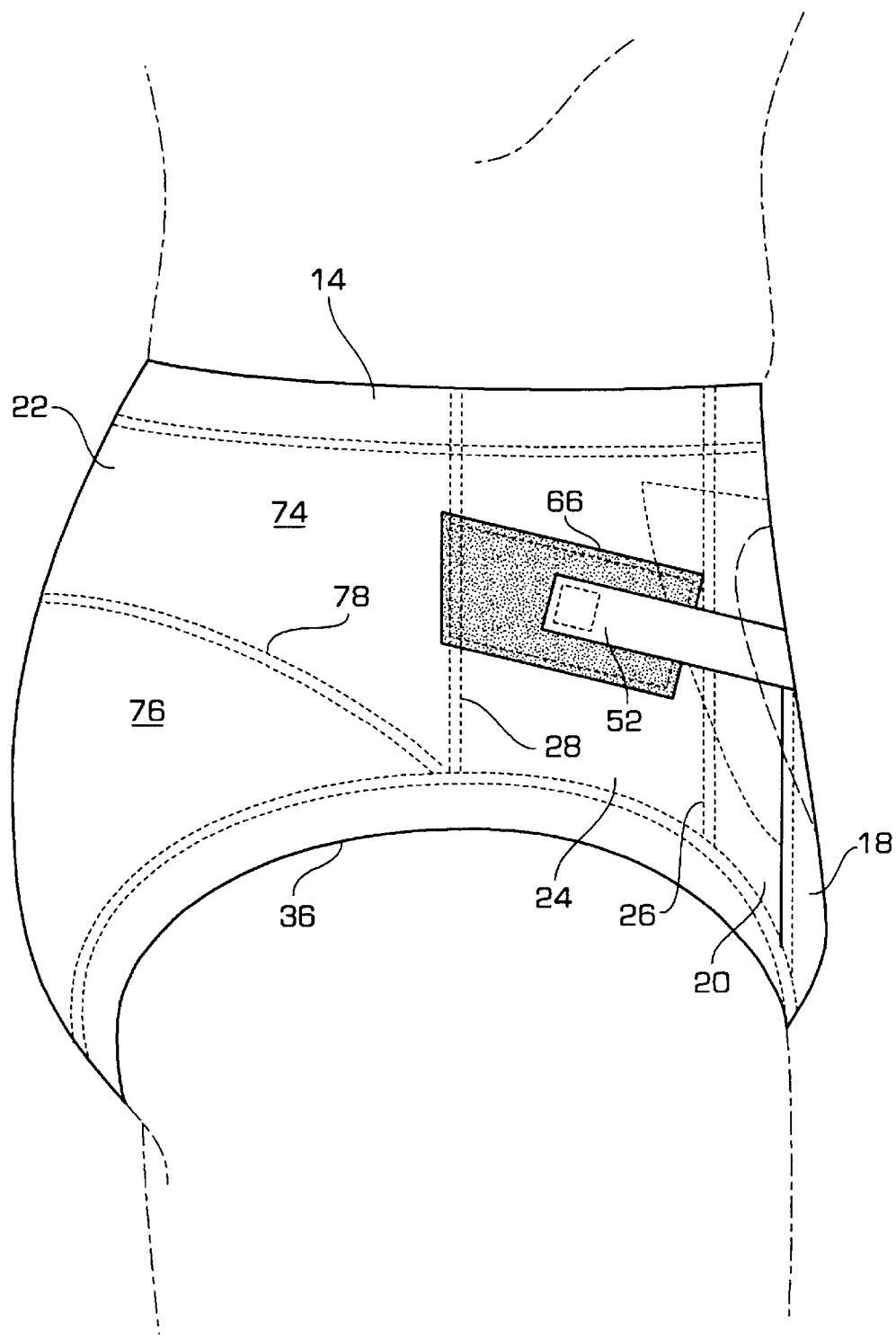
FIG. 2 is a side elevation view of the hernia brief of FIG. 1A shown on the body of a wearer depicted in broken lines.

The outer strap ends 58 and 60, and their attached securing patches 56, overlie the inner ends 62 and 64 of elongated fastening strips 66 and 68. The fastening strips 66 and 68 are formed of hook and loop fastening fabric which coordinates with the fabric of the securing patches 56 to provide an adjustable fastening for the distal ends 58 and 60 of the tension straps 52 and 54. The fastening strips 66 and 68 are secured to the forward half of the brief 12 in any convenient manner, as by sewing to the side panels 24 along seams 70 and 72. Referring to FIGS. 1A and 2, it is seen that the fastening strips 62 and 64 commence at the seams 26 between the front panel 20 and the side panels 24 and terminate at the seams 28 between the side panels 24 and the rear panel 22. As stated, these seams 28 are preferably disposed substantially along the lateral side centers of the hips of a wearer.

The fastening strips 66 and 68 are preferably wider than the tension straps 52 and 54 and their attached securing patches 56. This provides adjustability of fastening for the ends of the tension straps. The fastening strips 66 and 68 are elongated to provide independent individual adjustment for the tension in each tension strap. The fastening strips terminate at substantially the the lateral midpiont of the sides of the brief intermediate the length of the vertical seam 28 in FIG. 2. Fastening of the distal ends of the tension straps to the fastening strips is effected forward of oppositely disposed lateral side centers of the hips of the wearer. With this arrangement the tension in the tension straps is transferred to a distributed surface and area on the body of the user, and provides an unexpected degree of improved comfort when compared to prior devices. In particular this arrangement eliminates discomfort caused by body encircling straps, bands, and belts. FIG. 1A provides an illustration of one preferred embodiment of the invention using a pair of straps having inner ends secured to the front portion near the lateral center thereof and extending in substantially opposite directions therefrom with distal ends adjustably and independently secured to the side portions forward of oppositely disposed lateral side centers of the hips of the wearer for adjusting the tension in said straps for directing hernia retaining force toward the body of the wearer.

Figure 3:
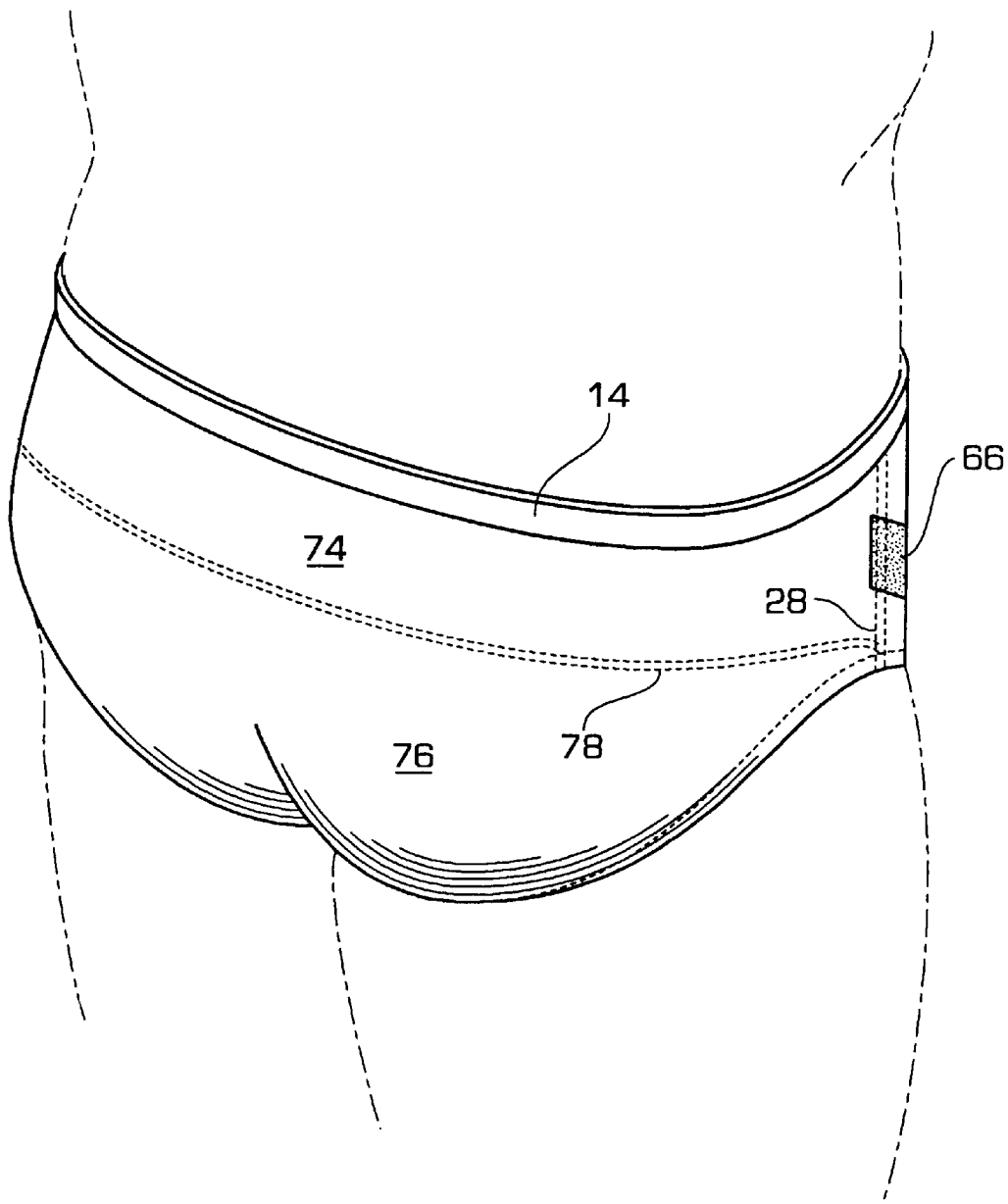
FIG. 3 is a side elevation perspective view of the combination hernia brief of FIGS. 1A and 2 on the body of a wearer, shown from the rear and side.

Referring to FIGS. 2 and 3, there is shown one preferred embodiment of the invention wherein the rear panel 22 is comprised of an upper section 74 and a lower section 76. These two sections 74 and 76 are joined by a transverse seam 78, which may conveniently be formed by sewing. In this embodiment the upper rear panel section 74 is formed of a heavier material than the lower rear panel section 76 to provide additional back support and to better distribute the tension conveyed by the fastening strips 66 and 68. As previously indicated, the rear panel 22, as well as the rest of the brief, is preferably formed of a supportive elastic material, such as SPANDEX.

It will be readily seen by one of ordinary skill in the art that the present invention fulfills the objects and objectives set forth above. After reading the foregoing specification, one of ordinary skill will be able to effect various changes, substitutions of equivalents and various other aspects of the invention as broadly disclosed herein. It is therefore intended that the protection granted hereon be limited only by the definition contained in the appended claims and equivalents thereof.

What is claimed:

1. A hernia brief comprising:

an undergarment brief having front, side, rear and crotch portions with spaced leg openings separated by parts of said rear and crotch portions;

said front portion having at least one truss pad supported therefrom and protruding inwardly of said brief to engage and support an abdominal hernia area of the body of a wearer;

a pair of straps having inner ends secured to said front portion near a lateral center thereof and extending in substantially opposite directions therefrom with distal ends adjustably and independently secured to said side portions forward of oppositely disposed lateral side centers of the hips of the wearer for adjusting the tension in said straps for directing hernia retaining force towards the body of the wearer.

2. A hernia brief according to claim 1 wherein:

said rear and side portions are secured to one another substantially at said oppositely disposed lateral side centers of the hips of the wearer.

3. A hernia brief according to claim 2 wherein:

said rear portion comprises an upper and a lower section, said sections extending substantially horizontally with said upper section being attached to said side portions and being of a heavier material than said lower section, whereby tension from said straps is transferred to opposite sides of said upper section.

4. A hernia brief according to claim 3 wherein:

said distal ends are secured to said side portions by means which include hook and loop fabric fastening patches on said distal ends secured to mating loop and fabric strips on said side portions.

5. A hernia brief according to claim 1 wherein:

said front portion comprises a front panel, said side portions comprise side panels, and said rear portion comprises a rear panel, said front, side and rear panels having upper edges attached to an elastic waistband, said side and rear panels having lower edges defining major portions of the perimeters of said leg openings, said crotch portion comprising a pouch having a lower transverse edge attached to a lower central transverse edge of said rear panel extending between said leg openings, said pouch having lower, intermediate and upper side edges, said front panel having a lower edge, said intermediate side edges of said pouch being attached to laterally spaced points on said lower edge of said front panel, said lower side edges of said pouch extending forward from said attachment of said lower transverse edge of said pouch to said lower central transverse edge of said rear panel to define portions of the perimeters of said leg openings extending between said lower central transverse edge of said rear panel and said points of attachment of said intermediate side edges of said pouch to said lower edge of said front panel, said upper side edges of said pouch extending upwardly from said points of attachment to said lower edge of said front panel and tapering inwardly therefrom to terminate in an apex secured to said front panel, said side edges of said pouch being unattached between said attachment at said apex and the points of attachment to said lower edge of said front panel to provide access openings into said pouch, said inner ends of said pair of straps being secured to said front portion substantially at the attachment of said pouch apex to said front panel, said rear and side panels being secured to one another substantially at oppositely disposed lateral side centers of the hips of the wearer, said loop and fabric strips on said side portions being attached to said side panels and extending from said lateral side centers forwardly on said side panels to said front panel.

6. A hernia brief according to claim 5 wherein:

said rear panel comprises an upper and a lower section, said sections extending substantially horizontally with said upper section being attached to said side panels and being of a heavier material than said lower section, whereby tension from said straps is transferred to opposite sides of said upper section.

7. A hernia brief comprising:

an undergarment brief having front, side, rear and crotch panels with spaced leg openings separated by depending extensions of said rear and crotch panels, said rear and side panels being secured to one another at seams substantially at oppositely disposed lateral side centers of the hips of a wearer, said front and side panels being secured to one another at spaced seams over the abdomen of said wearer, said front, side and rear panels having upper edges attached to a waistband, said front panel having at least one truss pad supported therefrom and protruding inwardly of said brief to engage and support an abdominal hernia area of the body of a wearer, a pair of straps having inner ends secured to said front panel substantially at a lateral center thereof and extending in substantially opposite directions therefrom with distal ends adjustably and independently secured to said side panels forward of said oppositely disposed lateral side centers of the hips of the wearer for adjusting the tension in said straps for directing hernia retaining force towards the body of the wearer, said rear panel having upper and lower portions extending around the posterior of a wearer with the upper portion extending to said waistband and said lower portion carrying said depending extension of said rear panel separating said leg openings, said upper portion of said rear panel having side edges forming said side seams attached to said side panels for transferring and distributing tension transferred by said straps, said upper and lower portions of said rear panel being secured together by a transverse seam, said crotch panel comprising a pouch having a lower transverse edge of said depending extension thereof attached to a lower central transverse edge of said depending extension of said rear panel, said pouch having lower, intermediate and upper side edges, said front panel having a lower edge, said intermediate side edges of said pouch being attached to laterally spaced points on said lower edge of said front panel, said lower side edges of said pouch extending forward from said attachment of said lower transverse edge of said pouch to said lower central transverse edge of said rear panel to define portions of the perimeters of said leg openings extending between said lower transverse edge of said rear panel and said points of attachment of said intermediate edges of said pouch to said lower edge of said front panel, said upper side edges of said pouch extending upwardly from said points of attachment to said lower edge of said front panel and tapering inwardly therefrom to terminate in an apex secured to said front panel, said side edges of said pouch being unattached between said attachment at said apex and the points of attachment to said lower edge of said front panel to provide dual access openings into said pouch.

8. A hernia brief according to claim 7 wherein:

said distal ends are secured to said side portions by means which include hook and loop fabric fastening patches on respective said distal ends secured to mating loop and fabric strips on said side portions extending from said lateral side centers forwardly on said side panels to said front panel.

9. A hernia brief according to claim 8 wherein:

said transverse seam joining said upper and lower portions of said rear panel extends between the lower termini of said side seams between said side and rear panels.

10. A hernia brief according to claim 9 wherein:

said truss pad is supported from said front panel by a pocket panel attached to said front panel.and.forming a pair of pockets symmetrically disposed over the abdomen area of the body of a wearer.

* * * * *